United States Patent [19]

Lover et al.

[11] 4,126,700
[45] Nov. 21, 1978

[54] AMINOPROPIONIC-ACIDS AS ECTOPARASITICIDES

[75] Inventors: Myron J. Lover, Mountainside; Arnold J. Singer, South Orange; Donald M. Lynch, Waldwick; William E. Rhodes, III, Cranford, all of N.J.

[73] Assignee: Block Drug Company, Inc., Reed & Carnrich Division, Kenilworth, N.J.

[21] Appl. No.: 796,545

[22] Filed: May 13, 1977

[51] Int. Cl.$^2$ .............................................. A01N 9/20
[52] U.S. Cl. ..................................................... 424/319
[58] Field of Search .......................................... 424/319

[56] References Cited
PUBLICATIONS

Trager; C. A. vol. 66 (1967), 27515w.
Decker et al., C. A. vol. 66 (1967), 20,247b.
Chesebrough–Pond's, Inc.; C. A. vol. 63 (1965), 4092d.
Labots et al.; C. A. vol. 64 (1966), 3988e.

*Primary Examiner*—Allen J. Robinson
*Attorney, Agent, or Firm*—Ostrolenk, Faber, Gerb & Soffen

[57] ABSTRACT

Certain aminopropionic acids have been found to exhibit ectoparacitisidal activity.

7 Claims, No Drawings

AMINOPROPIONIC-ACIDS AS ECTOPARASITICIDES

BACKGROUND OF THE INVENTION

Drugs presently used in treatment of human or animal ectoparasitic infestations are either dermal irritants or contain as active ingredients components having at least a potential liability for neurotoxic side effects to the host.

Preparations which are not strongly ovicidal need to be reapplied as successive hatchings occur. The ideal drug for treatment of ectoparasites should be active against the ova as well as the adult and nymphal forms, and should be relatively non-toxic to the host.

In contrast to drugs used by inunction, compositions designed to be used as shampoos or body washes must either exert their parasiticidal and ovicidal effects within a very short time, or must resist washing off during the course of ablutions.

It has been found that certain aminopropionic acids, especially the N-alkyl aminopropionic acids, alone or in equilibrium with their salts, fulfill all of these criteria. The aminopropionic acids are well known materials. They have heretofore been used as surface active agents and have been incorporated in cosmetic preparations as such. For example, a "cosmetic" type of liquid shampoo containing 10% of the sodium salt of N-Coco-$\beta$- aminopropionic acid, 8.25% triethanolamine lauryl sulfate, 2.5% of coconut diethanolamide, sufficient lactic acid to adjust the pH to 4.5–5.0, perfume, color and water q.s. ad. 100% is known. This shampoo is not known to be an ectoparasiticide.

It is the object of this invention to provide new safe and effective toxicants for lice, mites, other insects and their ova. This and other objects of the invention will become apparent to those skilled in the art from the following detailed description.

SUMMARY OF THE INVENTION

This invention relates to ectoparasiticidal toxicants and a method of controlling ectoparasites. More particularly, the invention relates to the use of certain aminopropionic acids as toxicants for lice and scabies and/or their ova and to toxicant compositions containing such acids.

DESCRIPTION OF THE PREFERRED EMBODIMENTS

The toxicants of the instant invention are those N-substituted -$\beta$-aminopropionic acids in which the N-substituent is derived from a fatty material. Thus, the N-substituted group is preferably an alkyl group which can contain 8 to 24 carbon atoms, preferably 10 to 18 carbon atoms and most preferably about 12 carbon atoms. N-coco-$\beta$-aminopropionic acid and N-lauryl-myristyl-$\beta$-aminopropionic acid are typical examples of the toxicants of this invention.

The amphoteric surfactant materials of the present invention have been used heretofore in certain shampoo formulations as foaming, cleansing and conditioning agents usually at a concentration of 10% or less. In such formulations, the aminopropionic acids are not generally pediculicidal or ovicidal. In order that the acids exhibit the desired activity, it is necessary that the formulation in which they are used have a pH on the acid side, that is, less than 7.0, preferably 6.8 or less. It is preferred to maintain the pH at about 3.0 or above and it has been observed that maximum activity occurs at a pH value in the neighborhood of 4. It is also necessary that shampoo formulations in which the aminopropionic acids are used do not contain a strong detergent. For example, the cosmetic shampoo formulation referred to earlier under the Background of the Invention does not contain an effective toxic amount of the aminopropionic acid, as defined herein, because of the presence of the triethanolamine lauryl sulfate. The lauryl sulfate tends to remove the active residue which would otherwise continue to act on the lice or their ova.

One or more of the toxic aminopropionic acids of the present invention can be incorporated into an active toxicant composition which can be in the form of a liquid, powder, lotion, cream, gel or aerosol spray, or foam as the result of formulation with inert pharmaceutically acceptable carriers by procedures well known in the art. Any pharmaceutically acceptable carrier, whether aqueous or not aqueous, which is inert to the active ingredient can be employed. By inert is meant that the carrier does not have a substantial detrimental effect on the pediculicidal or ovicidal toxicant activity of the active ingredient, or does not strongly promote the removal of the active ingredient upon rinsing.

The active aminopropionic acids are incorporated into the toxicant composition used to treat the substrate in need of such treatment, believed to be in need of such treatment, or desired to be prophylactically protected in an effective toxicant amount. By such amount is meant the amount which will cause at least 50% (for lotions) and 75% to 100% (for shampoos) of the ectoparasites exposed in the two minute immersion tests described below to die within 24 hours in the case of lice and within 2 weeks in case of the ova. This test is realistic for shampoos, and very severe but meaningful for drugs which are allowed to remain on the skin. The minimum concentration of aminopropionic acid in the composition required to provide an effective toxic amount varies considerably depending on the particular aminopropionic acids, the particular inert pharmaceutically acceptable carrier being employed and any other ingredients which are present. Thus, in one case a 10% concentration may suffice, while in other cases, concentrations as high as 25% may be required to obtain an effective toxic dose. Usually, the aminopropionic acids will be used in concentrations of about 5 to 25% and most preferably at concentrations of about 10 to 20%.

The instant aminopropionic acids can also be employed as an adjunct toxicant in a preparation which otherwise exhibits pediculicidal and/or ovicidal activity. In such preparations, the term "effective toxic dose" means that amount which will increase the mortality rate by at least about 20% in the standard immersion tests.

The pH of the formulation in which the aminopropionic acid is used can be adjusted by any known and convenient means such as, for example, by the use of an appropriate acid, ion exchange resin, etc.

The two minute immersion tests referred to above are carried out as follows:

Pediculicidal activity: A 50 ml beaker is filled with tap water and allowed to come to room temperature (about 24° C.). Ten young adult male and ten young adult female lice (*Pediculus humanus corporis*) of the same age group and from the same stock colony are placed on a 2×2 cm coarse mesh patch. The sample to be tested, maintained at room temperature, is shaken until homogeneous and placed into a 50 ml beaker. The mesh patch is placed into the sample immediately after pouring, allowed to submerge, and after two minutes is removed and immediately plunged into the beaker containing the tap water. The patch is vigorously agitated every ten seconds and after one minute the patch is removed and placed on paper toweling. The lice are then transferred to a 4×4 cm black corduroy cloth patch and this point of time is considered zero hours. Thereafter, the corduroy patch is placed in a petri dish which is covered and stored in a 30° C. holding chamber.

Ovicidal activity: 15 adult, 5 to 10 day old, female lice (*Pediculus humanus corporis*) are placed on a 2×2 cm nylon mesh patch which is placed in a petri dish, covered and maintained in an incubator at 30° C. for 24 hours. The adult lice are then removed and the number of plump, viable eggs and shriveled nonfertile eggs on the patch are recorded. The sample to be tested, maintained at room temperature, is shaken until homogeneous and poured into a 50 ml beaker. Immediately after the pouring, the mesh patch is placed into the beaker, allowed to submerge, and after two minutes is removed and immediately plunged into a 50 ml beaker containing tap water at room temperature (about 24° C.). The patch is vigorously agitated every ten seconds and after one minute, the patch is removed and placed on paper toweling for one minute. The patch is then placed in a petri dish which is covered and stored in the 30° C. incubator. Fourteen days following treatment, the number of hatched eggs and the number of shriveled or unhatched eggs is noted.

In both the pediculicidal and ovicidal two minute immersion tests, controls are run in identical manners to that described with room temperature (24° C.) tap water substituted for the sample to be tested. The results of the tests reported are net results.

In Table 1, the results of pediculicidal and ovicidal testing for toxicants of this invention are set forth. For comparative purposes, results achieved with the acids at a basic or substantially neutral pH (in the form of the sodium or triethanolamine salt) are also set forth. The compounds were tested in the form of 20 weight percent solution in water at the indicated pH.

Table 1

| Compound | pH | Mortality, % Pediculicidal | Ovicidal |
|---|---|---|---|
| N-Coco-$\beta$-aminopropionic acid | 4 | 100 | 100 |
| N-Coco-$\beta$-aminopropionic acid | 6.2 | 100 | 28 |
| N-Coco-$\beta$-aminopropionic acid sodium salt | 12.5 | 5 | 20 |
| N-Lauryl-myristyl-$\beta$-aminopropionic acid | 4 | 100 | 100 |
| N-Lauryl-myristyl-$\beta$-aminopropionic acid | 5.3 | 100 | 10 |
| N-Lauryl-myristyl-$\beta$-aminopropionic acid triethanolamine salt | 7.5 | 15 | 0 |

The pediculicidal activity of two toxicants of this invention as a function of concentration was determined. Table 2 sets forth the results employing solutions of N-coco-$\beta$-aminopropionic acid in water and Table 3 sets forth the results using N-lauryl-myristyl-$\beta$-aminopropionic acid in water.

Table 2
Pediculicidal activity of N-Coco-$\beta$-Aminoproionic acid as a function of concentration.

| Concentration, % by Weight | Mortality, % |
|---|---|
| 5 | 40 |
| 10 | 95 |
| 20 | 100 |
| 30 | 100 |
| 40 | 100 |

Table 3
Pediculicidal activity of N-Lauryl-Myristyl-$\beta$-aminopropionic acid as a function of concentration

| Concentration, % by weight | Mortality, % |
|---|---|
| 5 | 45 |
| 10 | 95 |
| 20 | 100 |
| 30 | 100 |
| 40 | 100 |

As noted above, various end use formulations can be prepared. Some typical formulations are set forth below and the amounts recited are percentages by weight:

EXAMPLE 1

Clear liquid suitable for topical application as a lotion, cream or spray.

| Isopropanol | 55 |
|---|---|
| N-Coco-$\beta$-aminopropionic acid | 20 |
| Water | 25 |
| Hydrochloric acid q.s. to pH 4.0 | |

EXAMPLE 2

Clear shampoo

| Isopropanol | 25 |
|---|---|
| N-Lauryl-myristyl-$\beta$-aminopropionic acid | 20 |
| Triethanolamine lauryl sulfate | 8 |
| Water | 47 |
| Hydrochloric acid q.s. to pH 4.0 | |

EXAMPLE 3

Aerosol Spray

| Isopropanol | 46 |
|---|---|
| N-Coco-$\beta$-aminopropionic acid | 20 |
| Water | 24 |
| Hydrochloric acid q.s. to pH 4.0 | |
| Isobutane | 10 |

EXAMPLE 4

Quick breaking aerosol foam

| Isopropanol | 25 |
|---|---|
| N-Coco-$\beta$-aminopropionic acid | 20 |
| Polysorbate 80 | 1 |
| Water | 34 |
| Hydrochloric acid q.s. to pH 4.0 | |
| Isobutane | 15 |

EXAMPLE 5

Pediculicidal Gel

| | |
|---|---|
| Isopropanol | 25.00 |
| N-Lauryl-myristyl-$\beta$-aminopropionic acid | 20.00 |
| Carbomer 940 | 0.75 |
| Triethanolamine | 0.75 |
| Water | 53.50 |

EXAMPLE 6

Pediculicidal Powder

| | |
|---|---|
| Pyrophyllite | 85.0 |
| N-Coco-$\beta$-aminopropionic acid | 7.5 |
| Isopropanol | 7.5 |

EXAMPLE 7

Dual phase liquid which emulsifies on shaking

| | |
|---|---|
| N-Lauryl-myristyl-$\beta$-aminopropionic acid | 20 |
| Methyl paraben | 0.05 |
| Propyl paraben | 0.005 |
| Water | 79.945 |
| pH 4.0 | |

EXAMPLE 8

White lotion

| | |
|---|---|
| N-Coco-$\beta$-aminopropionic acid | 20 |
| Water | 80 |
| Acetic acid q.s. to pH 4.0 | |

Various changes and modifications can be made in the instant invention without departing from the spirit and scope thereof. The various embodiments disclosed herein were set forth for the purpose of further illustrating the invention but were not intended to limit it. Throughout this specification and claims, all temperatures have been set forth in degrees Centigrade and all parts and percentages by weight unless otherwise indicated.

We claim:

1. A method of controlling ectoparasites or their ova which comprises topically applying to a human or animal in need of such control, an effective toxic amount of at least one N-fatty-$\beta$-aminopropionic acid for a time sufficient to kill at least 50% of the lice or ova thereon, wherein said fatty substituent is an alkyl moiety containing 8 to 24 carbon atoms.

2. The method of claim 1 wherein said alkyl moiety contains 12 to 20 carbon atoms.

3. The method of claim 1 wherein said acid is N-Coco-$\beta$-aminopropionic acid.

4. The method of claim 1 wherein said acid is N-Lauryl-myristyl-$\beta$-aminopropionic acid.

5. The method of claim 1 wherein said acid is employed in combination with an inert pharmaceutically acceptable carrier, said combination having a pH of less than 7.

6. The method of claim 6 wherein said carrier is aqueous and said pH is about 3 to 6.8.

7. The method of claim 6 wherein said pH is about 4.

* * * * *